United States Patent
Yoshinaga et al.

(10) Patent No.: US 6,629,005 B2
(45) Date of Patent: Sep. 30, 2003

(54) METHOD OF CONFIGURING BLOOD CIRCUIT FOR MEDICAL APPLICATION AND CONFIGURATION APPARATUS THEREFORE

(75) Inventors: Kunio Yoshinaga, Hiroshima (JP); Hirosato Maehama, Hiroshima (JP); Noriaki Nakagawa, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 129 days.

(21) Appl. No.: 09/870,103

(22) Filed: May 30, 2001

(65) Prior Publication Data
US 2002/0013715 A1 Jan. 31, 2002

(30) Foreign Application Priority Data
Jun. 1, 2000 (JP) .......................... 2000-164267

(51) Int. Cl.[7] .................. G06F 19/00; A16M 1/14
(52) U.S. Cl. ................. 700/97; 700/90; 604/4.01; 210/143
(58) Field of Search .................. 700/90, 97; 604/48, 604/65, 4.01; 210/143

(56) References Cited

U.S. PATENT DOCUMENTS

| | | | | |
|---|---|---|---|---|
| 4,502,488 A | * | 3/1985 | Degironimo et al. | 600/505 |
| 4,769,134 A | * | 9/1988 | Allan et al. | 210/87 |
| 4,886,060 A | * | 12/1989 | Wiksell | 606/39 |
| 4,889,635 A | * | 12/1989 | Chevallet | 210/646 |
| 6,221,040 B1 | * | 4/2001 | Kleinekofort | 604/65 |

FOREIGN PATENT DOCUMENTS

JP  63-95063  4/1988

* cited by examiner

Primary Examiner—Jayprakash N. Gandhi
(74) Attorney, Agent, or Firm—Merchant & Gould P.C.

(57) ABSTRACT

In a method of configuring a blood circuit for medical application, one unit component is selected for each of the divided unit sections and the selected unit components are combined to configure a blood circuit component. A blood circuit system database in which data with respect to the unit sections and unit components are stored is used. On the basis of the database, the selected unit component input to the computer. An assembly drawing of the blood circuit obtained by combining the selected unit components, a full length and an amount of filled blood are displayed on a display by using the database. When the displayed assembly drawing etc. is not fit for the desired specification, the selection of the unit component is changed, so as to display again the assembly drawing etc. of the blood circuit.

7 Claims, 14 Drawing Sheets

FIG. 7A [A-1]
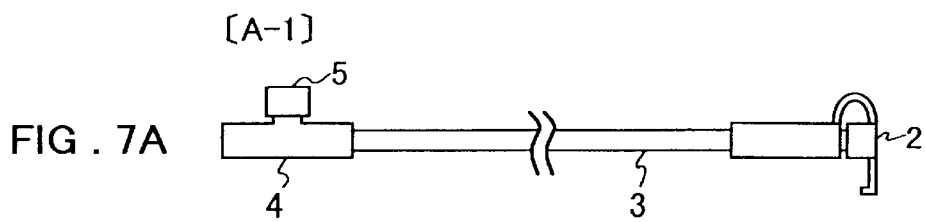
FIG. 7B
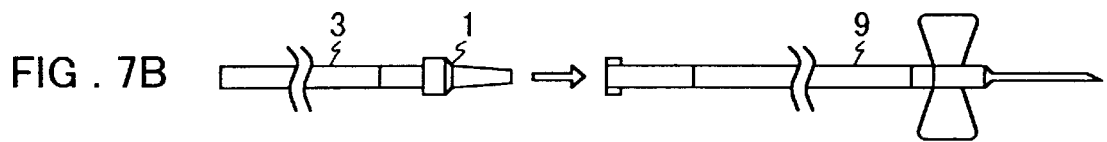
FIG. 7C
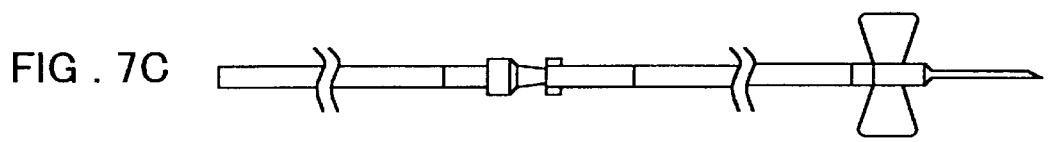
FIG. 7D [A-2]
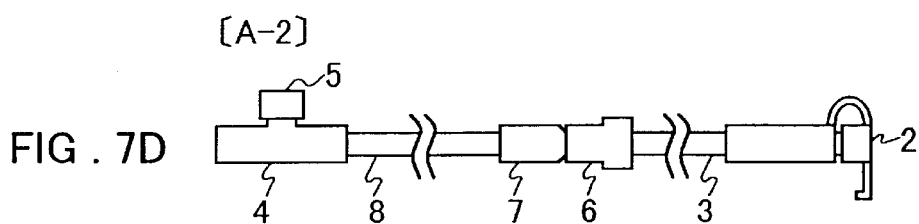
FIG. 7E
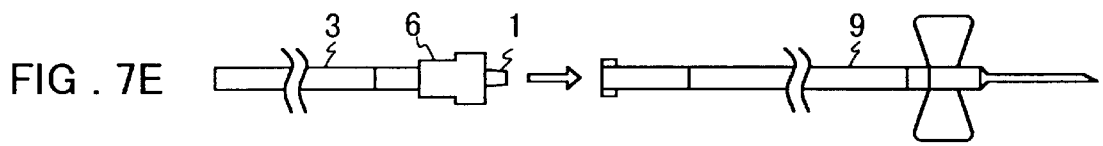
FIG. 7F
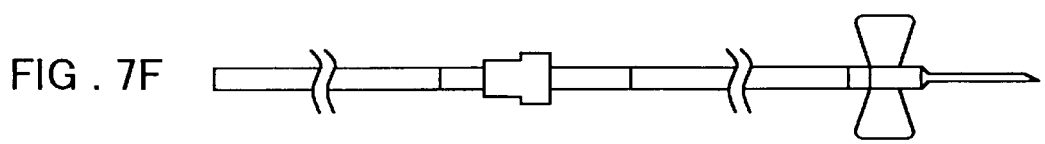

FIG. 8A    [B-1-1]
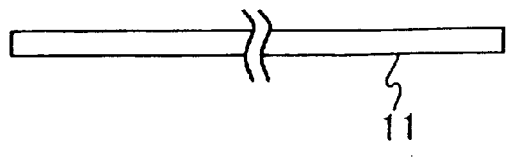
FIG. 8B    [B-1-2]
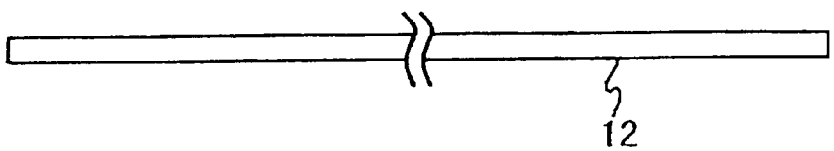
FIG. 8C    [B-2-1]
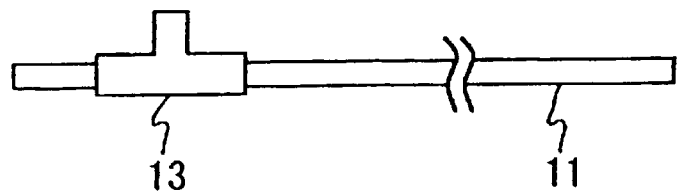
FIG. 8D    [B-2-2]
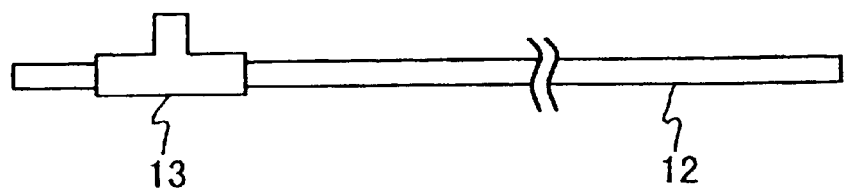

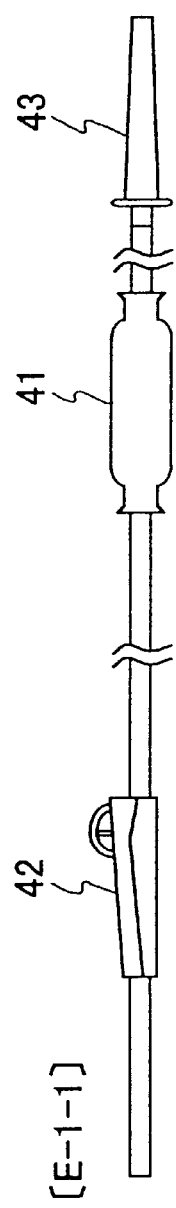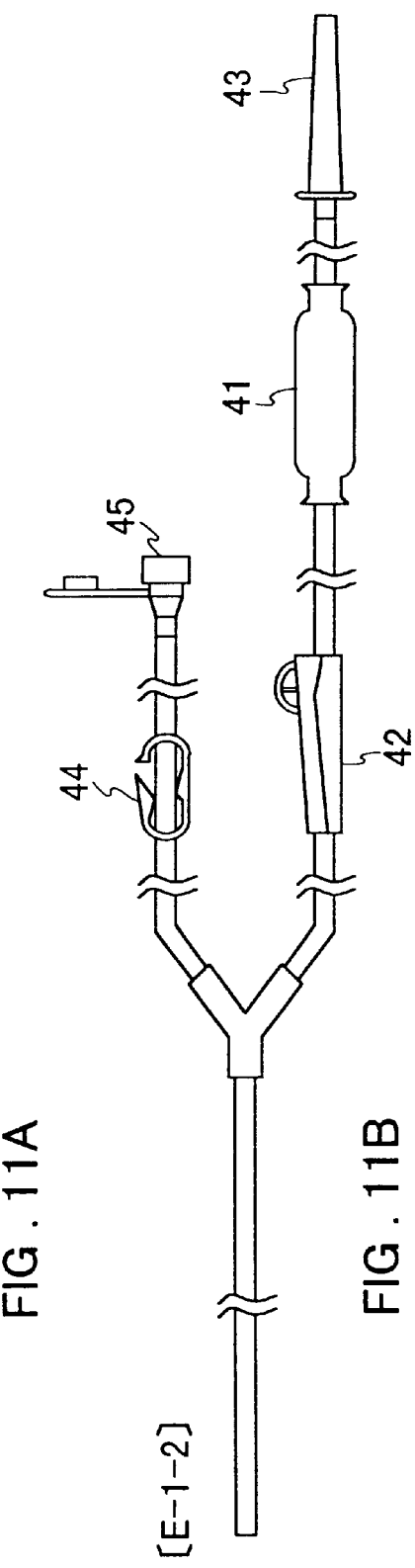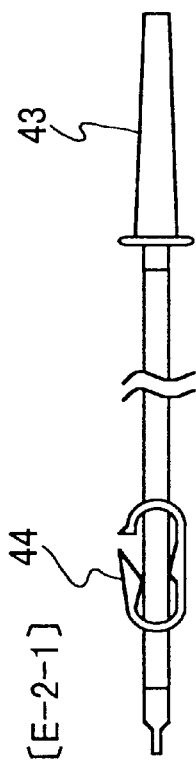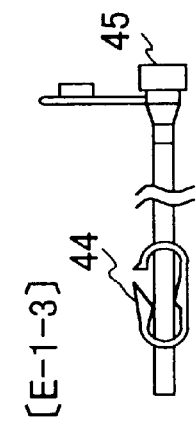
FIG. 11A
FIG. 11B
FIG. 11D
FIG. 11C

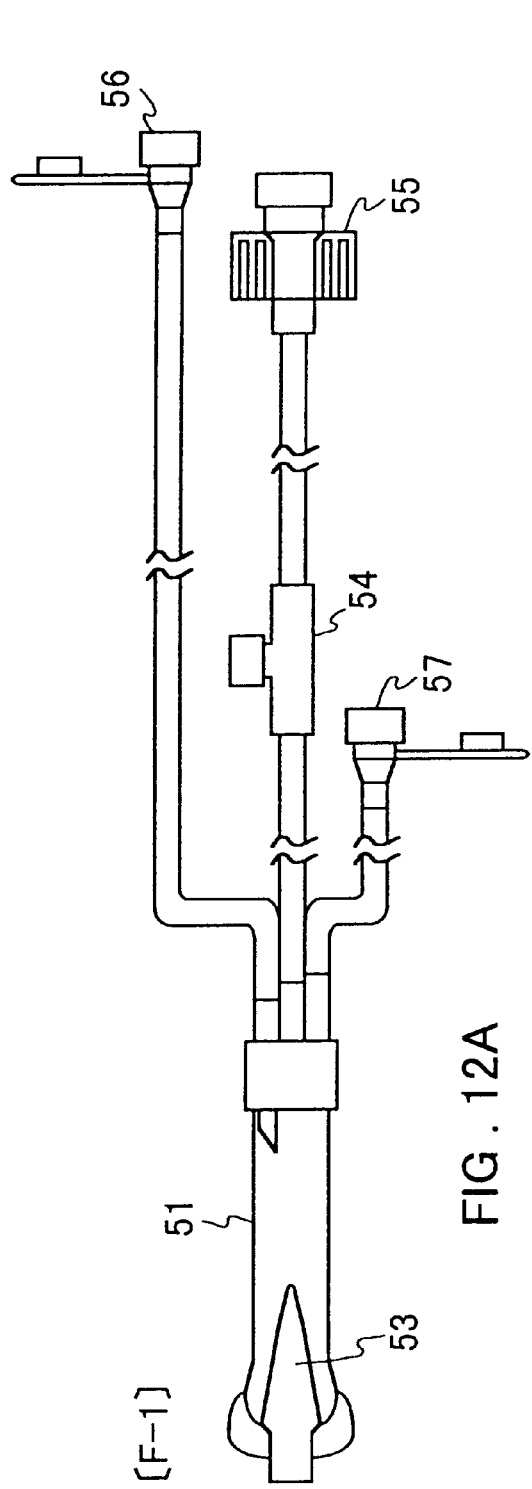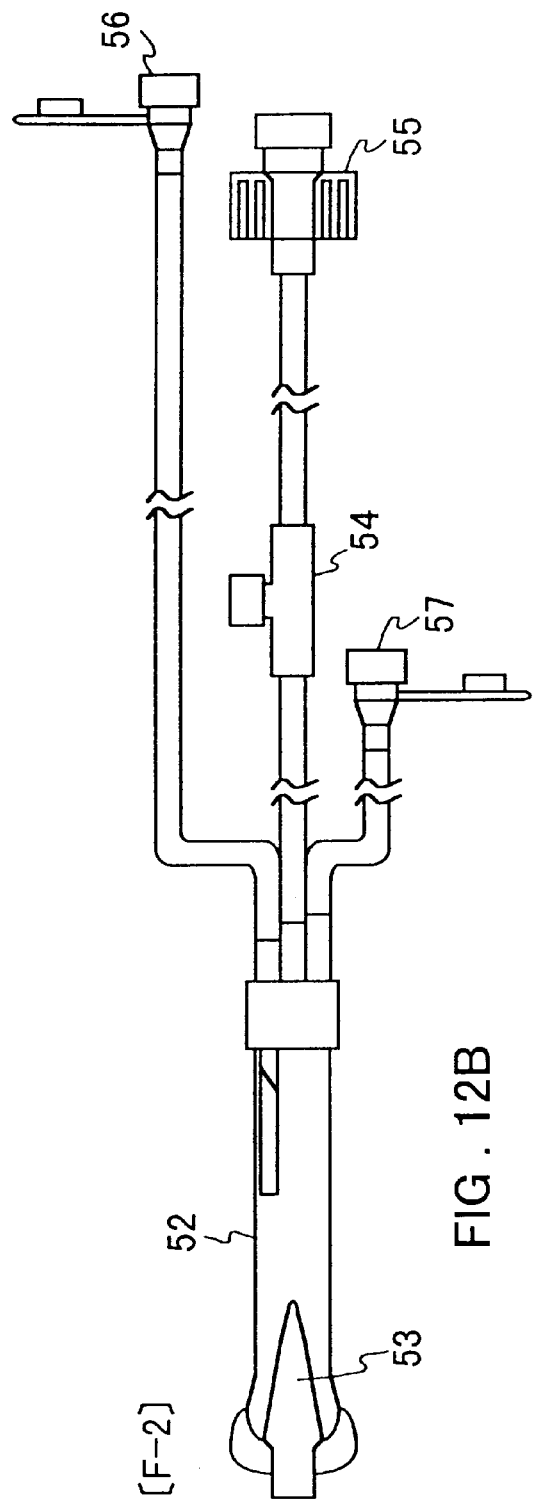
FIG. 12A
FIG. 12B

METHOD OF CONFIGURING BLOOD CIRCUIT FOR MEDICAL APPLICATION AND CONFIGURATION APPARATUS THEREFORE

FIELD OF THE INVENTION

The present invention relates to a method of configuring a blood circuit for medical application. In more detail, it relates to a method of configuring a desired blood circuit for medical application on a computer by systematizing many components constituting the blood circuit into a plurality of unit sections and selecting a component in each unit section.

BACKGROUND OF THE INVENTION

A blood circuit for medical application includes a blood circuit used for, for example, a dialysis. The dialysis requires not only a dialyzer but also a blood circuit for connecting a patient to the dialyzer. Conventionally, this blood circuit for dialysis varies in specifications depending upon users, i.e., hospitals, doctors, or laboratory technicians. That is, most of the conventional blood circuits are customized for individual users and do not have general versatility. Actually, a large number of different kinds of blood circuit systems are employed.

Since such blood circuits are customized for individual users, the cost is high and it takes a long time to deliver the products to users. In other words, it takes a long time to configure a circuit by repeating trials and errors, which may lead to increased cost. A more important problem is that a dialysis technique is dependent on the experience of in the individual person in charge such as a doctor, a laboratory technician, etc., and a method of connecting each machine to the circuit system and a method of using the circuit system are not systematized. Therefore, a circuit system may be changed subjectively by the individual person in charge. Furthermore, compatibility between different products is not established. Thus, there are problems in safety as a product used directly on the human body. Examples of such problems are a safety problem, for example, failure in fitting of a tool such as an indwelling needle, etc. that is connected to the circuit, and a lack of versatility, that is, because of a difference in length even on the order of only several centimeters, such an apparatus has to be produced based on a different standard.

On the other hand, with the stability of the performance of dialyzers in recent years, the safety of blood circuits, ease of using, and economical efficiency are becoming problems. In order to solve such problems, it is urgently demanded to standardize various components constituting a blood circuit and to provide the stability in quality, convenience, and rapidity in configuring a circuit.

With respect to the demand, JP63 (1988)-95063A proposes that each component is integrated into one piece of a packaged system. However, this proposal has disadvantages in that equipment being connected to the circuit system has less versatility, and that the system is not used conveniently.

Furthermore, there are about 3400 types of blood circuits only in Japan. Conventionally, problems with respect to the conveniences in using, for example, length, location of parts, etc., are adjusted by trial and error and samples are made and attached to a dialyzer. In other words, the adjustments have been carried out by using a real machine.

In order to make samples, it is necessary to make a standard drawing and often calculate the amount of filled blood or length based on the standard drawing. If defects are detected in the test by the use of real machines, there is a bother to start again from the formation of standard drawings.

SUMMARY OF THE INVENTION

It is an object of the present invention to provide a method of easily configuring a blood circuit for medical applications, which is capable of configuring a blood circuit in accordance with the applications.

It is another object of the present invention to provide a method of configuring a blood circuit for medical applications, which is capable of checking efficiently whether the circuit is fit for a desired specification or not, or capable of efficiently correcting the blood circuit configuration without actually assembling a sample, and an apparatus used for the configuring method.

In the method of configuring the blood circuit for medical application of the present invention, a blood circuit system is formed by dividing a blood circuit into a plurality of sections and preparing a plurality of selectable unit components for at least one unit section. By selecting at least one unit component from each unit section and combining the selected unit components, an individual blood circuit is configured. For configuration, the method includes using a blood circuit system database in which data with respect to the unit sections and the unit components contained in the blood circuit system are stored, inputting one of the unit sections on a basis of the blood circuit system database as an assigned unit section to the computer, extracting the data of a plurality of the corresponding unit components from the blood circuit system database by the computer based on the input assigned unit section and displaying the extracted data on a display, and inputting one component selected from the displayed unit components as a selected unit component to the computer. After carrying out the above-mentioned procedures in the necessary unit section, by the use of the blood circuit system database, an assembly drawing showing an entire configuration of the blood circuit obtained by combining the input selected unit components and at least one of a full length of the blood circuit or an amount of filled blood are displayed on a display. Then, a command for changing the selection of the unit components or a command for determining the configuration of the blood circuit is input to the computer.

According to this method, by only selecting the unit component in accordance with the unit section, it is possible to configure the blood circuit in accordance with the applications easily. Moreover, without constructing a real sample of the blood circuit, it is possible to check whether the circuit is fit for the desired specification or not. Furthermore, in a case where the sample is not fit for the desired specification, only by changing the selection of the unit components, it is possible to check whether the reconfigured sample is fit for the desired specification promptly. Since the blood circuit system can be produced by dividing a plurality of reasonable unit sections from the viewpoint of techniques in dialysis, it is possible to clarify individual features of each unit component. Therefore, it is useful to select unit components appropriately in accordance with the applications.

The above-mentioned method of configuring a blood circuit for medical application further includes, after the procedure of inputting the selected unit components to the computer, selectively either returning to the procedure for inputting the assigned unit section or inputting a selection terminating command for terminating the input of the selected unit components and going to the following procedures; when the selection terminating command is input, if there is any unit section with no selected unit component input, returning to the procedure of inputting the assigned unit section; and if the selected unit component has been input in all the unit sections, going to the following procedures, and if the selection of the unit component is to be changed, returning to the procedures of inputting the assigned unit section.

In the above-mentioned method, if the command of determining the configuration of the blood circuit is input, based on the blood circuit system database, the price of the blood circuit obtained by combining each selected unit component is displayed on the display.

Furthermore, it also is desirable that an existing standard database in which a plurality of existing standards are stored is used, the existing standard being a plurality of the combination of unit components constituting an existing specific blood circuit, and when an assembly drawing, a full length of the blood circuit and an amount of filled blood are displayed, the existing standard being analogous to the configuration of the displayed blood circuit is retrieved and displayed as an analogous standard. Thus, when the existing standard that complies with a desired specification is present, it is not necessary to produce a blood circuit based on a new standard, and thus, the blood circuit can be produced efficiently and economically.

Another method of configuring a blood circuit for medical application of the present invention includes a blood circuit system that is the same as the above, and uses a similar blood circuit system database. The method includes: inputting set conditions including a price with respect to the blood circuit to be configured to the computer; and extracting a predetermined range of candidates of the combinations of the unit components from the blood circuit system database based on the degree of the compliance with the input set conditions. A list of the candidates of the combinations of the extracted unit components is displayed on a display, and a selected assignment of one combination selected from the candidates of the displayed combinations is input to the computer. Next, an assembly drawing of an entire configuration of the blood circuit obtained by combining the selected unit components and at least one of a full length of the blood circuit or an amount of filled blood are displayed on the display in accordance with the input of the selected assignment by the use of the blood circuit system database.

According to this method, it is possible to determine the combinations of unit components constituting a blood circuit easily based on the set conditions from an economical viewpoint or a productive viewpoint.

In the above-mentioned method, it also is desirable that an existing standard database in which a plurality of the existing standards are stored is used, the existing standard being a plurality of the combination of the unit components constituting an existing specific blood circuit. When the candidates of the combinations of the unit components are extracted, an existing standard of the combination having a high degree of the compliance with the set conditions are extracted also from the existing standard database and added to the predetermined range of the candidates of the unit components.

A first apparatus for configuring a blood circuit for medical application of the present invention is an apparatus for configuring a blood circuit for medical application based on the blood circuit system, and includes the above-mentioned blood circuit system database. The apparatus further includes a unit section assignment portion for inputting one unit section on the basis of the blood circuit system database as an assigned unit section; a unit component display portion for extracting data of a plurality of the unit components corresponding to the input assigned unit section and displaying the extracted data; a unit component selection portion for inputting one unit component selected from the displayed unit components, maintaining the data of the selected unit component of all the unit sections, and supplying the maintained data as data of the combination of the selected unit components; and an assembly drawing etc. display portion for displaying an assembly drawing and at least one of a full length of the blood circuit or an amount of filled blood on the display. In the apparatus, the data of the selected unit component in the unit component selecting portion can be changed by assigning the unit section in the unit section assignment portion.

It is desirable that the apparatus having the above-mentioned configuration further includes an existing standard database in which a plurality of the existing standards are stored, the existing standard being the combination of the unit components constituting an existing specific blood circuit, an analogous standard retrieving portion for retrieving a blood circuit that is analogous to the combination of the selected unit components from the existing standard database on a basis of the data supplied from the unit component selection portion, and an analogous standard selection portion having a function of selecting one from the retrieved existing standards by the analogous standard retrieving portion, and instead of in the unit component selection portion, supplying the data of the combinations of the selected unit components on the basis of the selected existing standard to the assembly drawing etc. display portion.

A second apparatus for configuring a blood circuit for medical application of the present invention, similar to the first apparatus, is an apparatus for configuring a blood circuit based on the above-mentioned blood circuit system and includes: the above-mentioned blood circuit system database. Furthermore, the second apparatus includes a set conditions input portion for inputting the set conditions including a price with respect to the blood circuit to be configured; a retrieved combination candidate display portion for, by the use of the blood circuit system database, retrieving candidates of the combinations of the unit components based on the degree of the compliance with the input set conditions, extracting the predetermined range of the retrieved candidates of the combinations of the unit components, and displaying the extracted candidates of the combinations; a selection assignment portion for selecting and supplying one of the candidates of the combinations of the extracted unit components to an assembly drawing etc. display portion as data of the combinations of the selected unit components; and an assembly drawing etc. display portion for displaying an assembly drawing showing an entire configuration of the blood circuit and at least one of a full length of the blood circuit or an amount of filled blood on the display by the use of the blood circuit system database on the basis of the data of the combinations of the selected unit components.

It is desirable that the apparatus having this configuration further includes an existing standard database in which a plurality of the existing standards are stored, the existing standard being the combination of the unit components constituting an existing specific blood circuit, wherein the retrieved combination candidate display portion retrieves the existing standard database together with the blood circuit system database.

Furthermore, it is desirable that the apparatus for configuring the blood circuit includes the above-mentioned first apparatus and the second apparatus and includes an operation selection portion for selecting any one of an operation by the unit section assignment portion or an operation by the set conditions input portion.

In the method of configuring the blood circuit for medical application or a configuration apparatus mentioned above, the blood circuit for medical application is a blood circuit for dialysis and the blood circuit is divided into an artery side circuit and a vein side circuit, further each of the artery side circuit and the vein side circuit is divided into a plurality of unit sections.

BRIEF DESCRIPTION OF THE DRAWINGS

FIGS. 7A to 7F are plan views showing examples of unit components applied to a unit section A.

FIGS. 8A to 8D are plan views showing examples of unit components applied to a unit section B.

FIGS. 11A to 11D are plan views showing examples of unit components applied to a unit section E.

FIGS. 12A to 12B are plan views showing examples of unit components applied to a unit section F.

DETAILED DESCRIPTION OF THE INVENTION

First Embodiment

Figure 1:
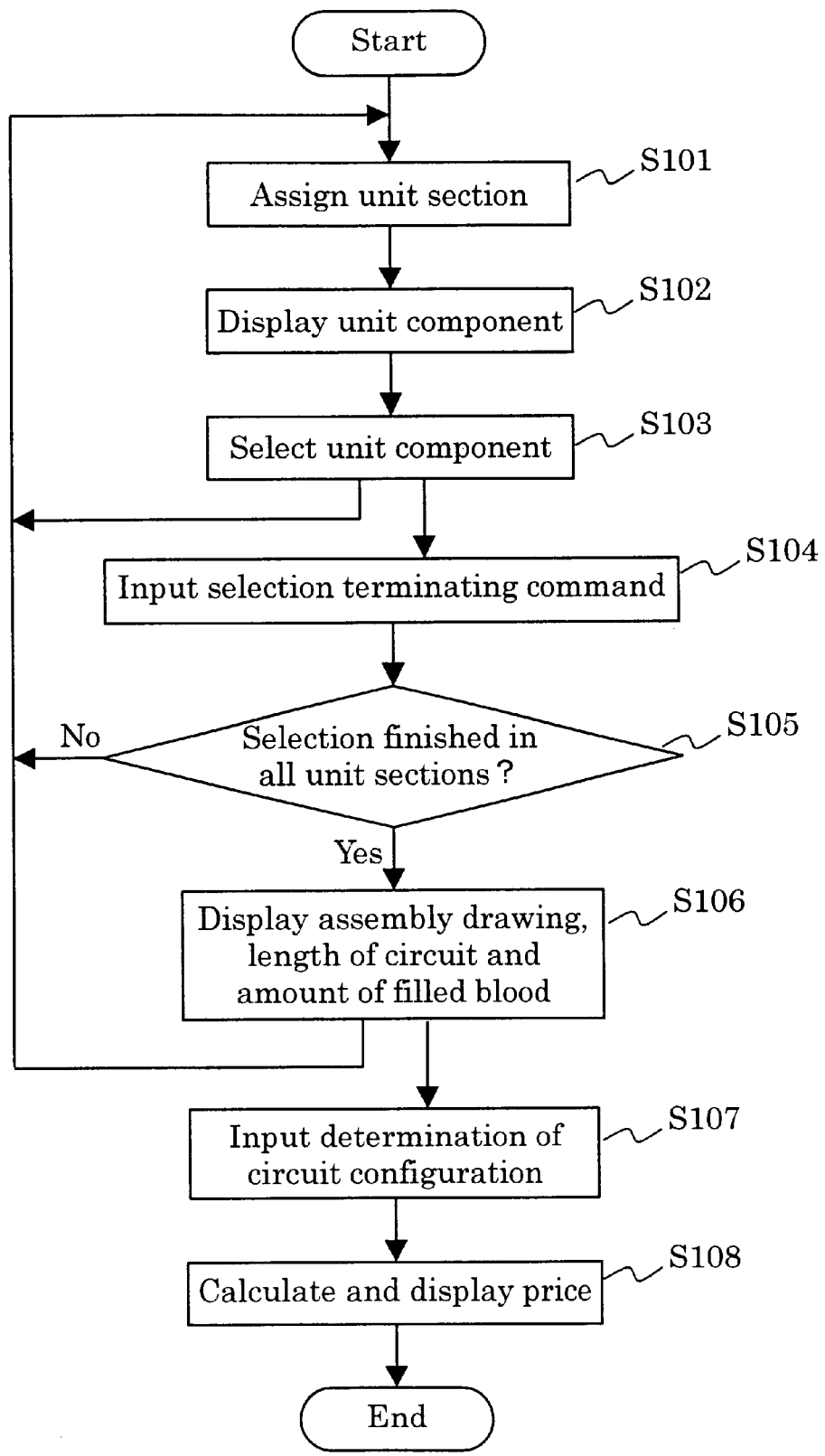
FIG. 1 is a flow chart showing a method of configuring a blood circuit for medical application according to a first embodiment of the present invention.

FIG. 1 is a flow chart showing a method of configuring a blood circuit for medical applications of a first embodiment. This method is employed for, for example, a blood circuit system shown in FIGS. 6 to 13.

Figure 6:
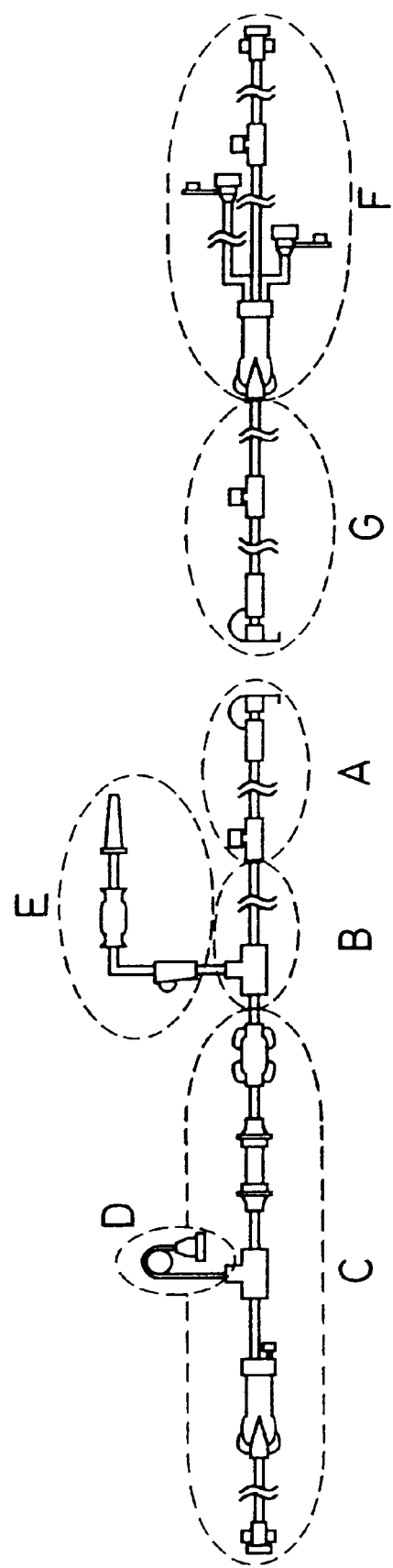
FIG. 6 is a plan view showing an example of unit sections of a blood circuit for medical application according to the present invention.
Figure 9A:
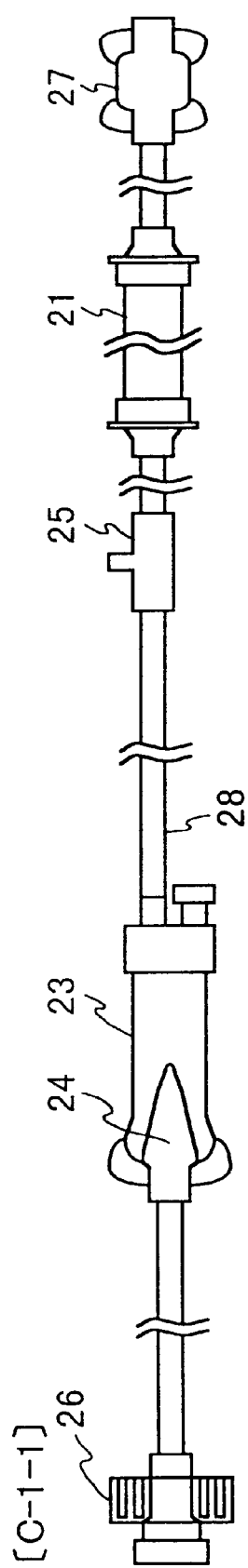
FIGS. 9A to 9D are plan views showing examples of unit components applied to a unit section C.
Figure 9B:
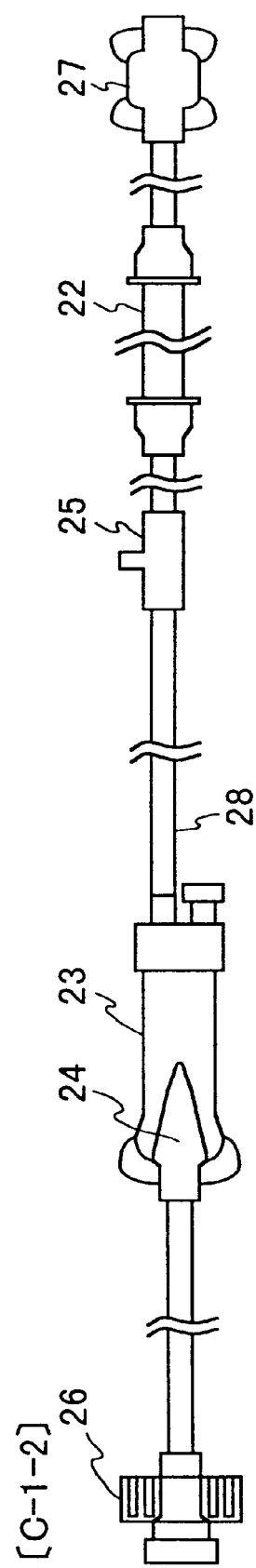
Figure 9C:
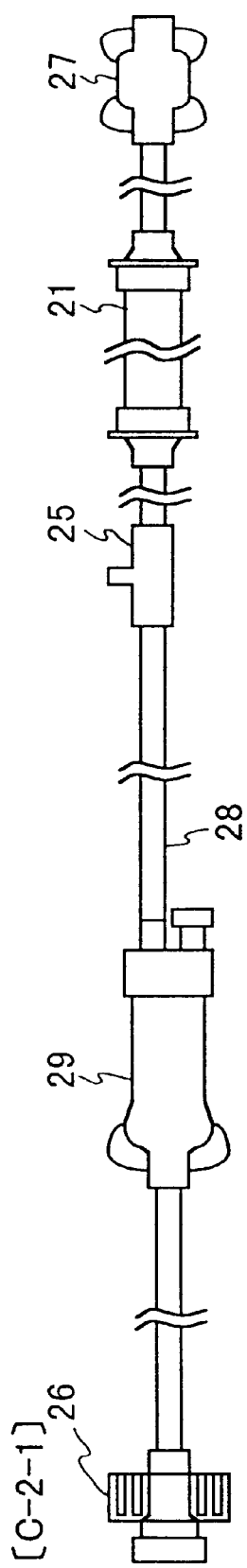
Figure 9D:
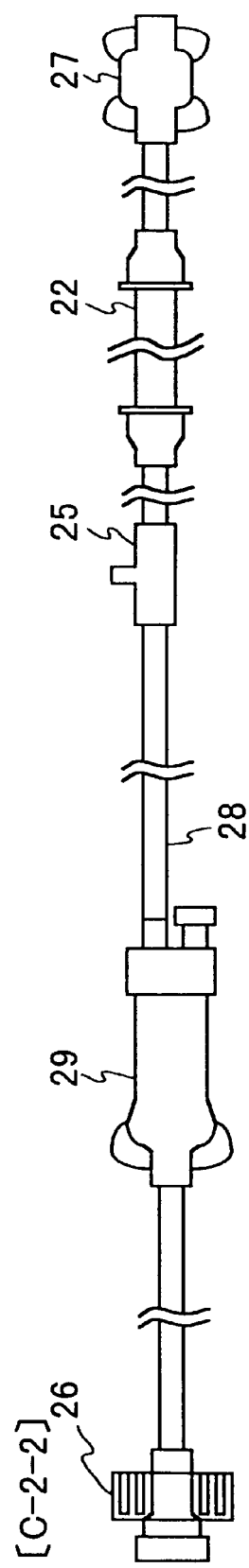

FIG. 6 shows one example of a formation of unit sections in a blood circuit system for dialysis. In this system, the blood circuit is divided into an artery side circuit and a vein side circuit. Each of the artery side circuit and the vein side circuit is further divided so as to form unit sections A to G. Herein, the artery side circuit denotes a circuit constituting a portion between a connection portion of an indwelling needle at the artery side and a connection portion of a dialyzer when a dialysis is carried out. On the other hand, the vein side circuit denotes a circuit constituting a portion between a connection portion of the dialyzer and a connection portion of an indwelling needle side at the vein side when dialysis is carried out. As shown in FIGS. 7 to 13, each unit section is provided with a plurality of selectable unit components, for example, a unit component A-1, a unit component A-2, etc. Each unit component is usually composed of a plurality of components. The definition of each unit section and the features of each unit section are described hereafter.

In the thus configured blood circuit system, at least one unit component is selected from the unit sections A to G, and the selected unit components are combined so as to configure a blood circuit. FIG. 1 shows a method of combining unit components efficiently and properly by the use of a computer in configuring the blood circuit in this way. This embodiment will be explained with reference to the blood circuit systems shown in FIGS. 6 to 13.

In order to carry out this configuring method, a blood circuit system database in which data with respect to unit sections and unit components contained in a blood circuit system are stored is constructed on a computer. The contents contained in the data includes, for example, a shape, size, data related to a production cost, etc. of each unit component classified in each unit section.

As shown in FIG. 1, first, by using a blood circuit system database, one section is selected from the unit sections A to G shown in FIG. 6 and the selected section is input to the computer as an assigned unit section (step S101). Based on the input assigned unit section, a plurality of the corresponding unit components are retrieved from the blood circuit system database and displayed on a display (step S102). One unit component is selected from the displayed unit components and input as the selected unit component (step S103).

Next, selection is carried out between returning to step S101 or going to step S104.

In the case of returning to step S101, the selected unit component is input by assigning an unselected unit section in which no selected unit component is input. In this way, one unit component is selected appropriately in each unit section from a plurality of the stored unit component data. By repeating this procedures, unit components are selected for all the unit sections A to G. Alternately, it is also possible to assign the previously selected unit section again so as to change the selection of unit components.

In step S104, a selection terminating command is input for terminating the input of the selected unit components. When the selection terminating command is input, the processing splits depending upon whether an unselected unit section is present or not (step S105). When an unselected unit section is present, the processing is returned to the procedure for inputting the assignment of the unit section (step S101), and when the selected unit component is input for all the selected unit sections, the processing goes to the following procedure (step S106).

In step S106, based on the blood circuit system database, an assembly drawing showing an entire configuration of the blood circuit in which the selected unit components are combined, and a full length of the blood circuit and the amount of filled blood are displayed on a display. The assembly drawing, the full length of the blood circuit and the amount of filled blood are formed or calculated each time based on the data of each unit component. Alternately, it is possible to prepare in advance, all the sets of an assembly drawing, a full length of the blood circuit and the amount of filled blood corresponding to all the combinations of the unit components and display one of the sets according to the selected unit components. Among the contents to be displayed, the assembly drawing is essential, but at least one of the full length and the amount of filled blood may be displayed together with the assembly drawing.

Next, a processing is selected based on whether the configuration of the displayed blood circuit is corrected or not, i.e., the selected unit components are changed or not. Whether the configuration of the blood circuit is corrected or not is judged by verifying conditions, for example whether the constructed blood circuit has a length fit for the dialyzer to be used or not, or the amount of filled blood is appropriate or not, etc. Therefore, in step S106, as the full length and the amount of filled blood are displayed together with the assembly drawing, the verification can be carried out efficiently. Furthermore, in addition to the above-mentioned items, if the total weight, volume (bulk) and the like are displayed, it is possible to consider so as to allow the amount of waste to be reduced.

When the configuration of the blood circuit is to be corrected, the above-mentioned procedures are repeated by returning to the procedure for inputting the assignment of a unit section (step S101). When the configuration of the blood circuit is not to be corrected, a command for determining the configuration of the blood circuit is input to the computer (step S107). When the command of determining the configuration of the blood circuit is input, based on the blood circuit system database, the price of the blood circuit in the combination of selected unit components is calculated and displayed on the display (step S108). Thus, it is possible to investigate the constructed blood circuit from the economical aspect. However, step 108 is not an essential step for this embodiment.

According to the above-mentioned method, by only selecting the unit component with respect to the unit section, it is possible to configure the blood circuit in accordance with the applications easily. Moreover, without constructing the sample actually, it is possible to check whether the circuit is fit for the desired specification or not. Furthermore, if the circuit is not fit for the desired specification, only by changing the selection of the unit component for a part of the unit section, the compliance with the reconfigured blood circuit can be checked promptly.

Moreover, it is more effective to construct and use an existing standard database in addition to the blood circuit system database. The existing standard is defined as the combination of the unit components constituting the existing specific blood circuit. The existing standard database is constructed by storing a plurality of such existing standards. Thus, for example, the existing standard analogous to the configuration of the blood circuit displayed in step S106 is retrieved and displayed as an analogous standard. If the analogous standard is highly compliant with the desired specification, instead of configuring a new blood circuit, the existing blood circuit is selected. Therefore, since it is not necessary to make a new standard, and it is possible to provide a blood circuit more efficiently and more economically.

Figure 2:
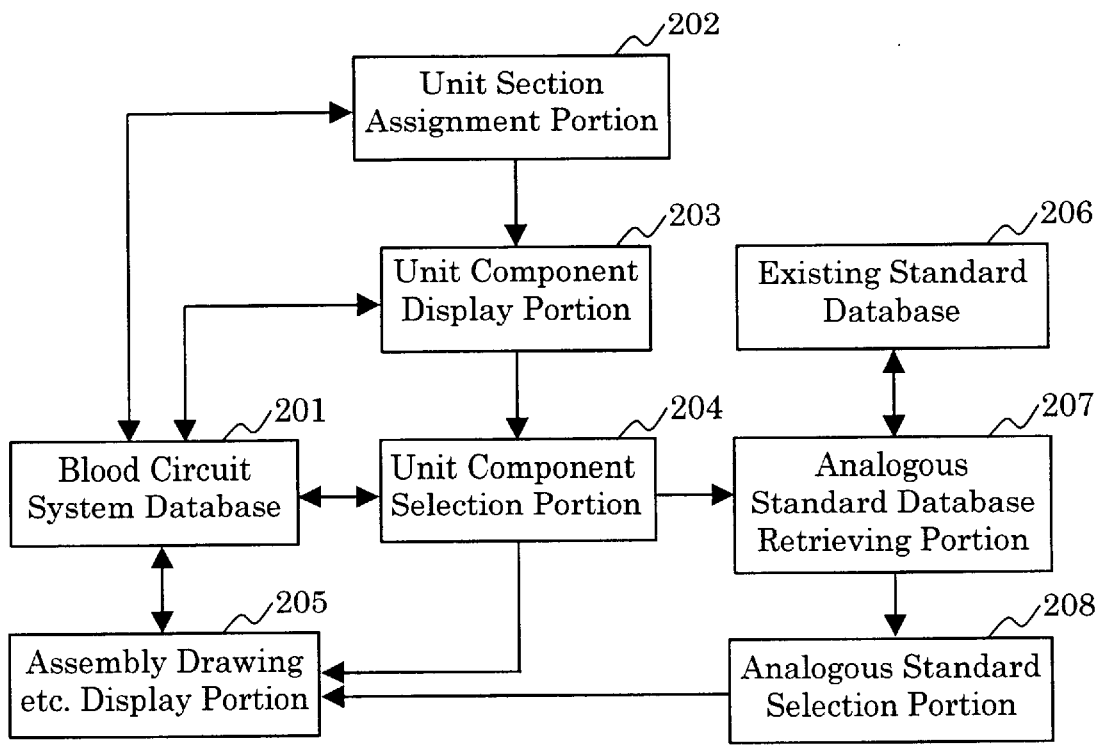
FIG. 2 is a block diagram showing an apparatus for configuring a blood circuit for medical application according to the first embodiment of the present invention.

FIG. 2 shows an apparatus for configuring a blood circuit for medical applications for carrying out the above-mentioned method. Numeral 201 denotes a blood circuit system database. A unit section assignment portion 202 has a function of inputting one of the unit sections based on the blood circuit system database 201 as a assigned unit section. In a unit component display portion 203, data of a plurality of unit components corresponding to the input assigned unit section are extracted from the blood circuit system database 201 and displayed on a display (not shown). A unit component selection portion 204 has a function of selecting one of the unit components, displayed by the unit component display portion 203, inputting the selected component and maintaining the data of the selected unit component for all the unit sections. By repeating the procedures by the unit section assignment portion 202, the unit component display portion 203 and the unit component selection portion 204, the selection of the unit component is carried out for all the unit sections. The change of the unit component that was once selected is carried out by assigning the unit section to be changed again by the unit component assignment portion 202. The selected data maintained in the unit component selection portion 204 is supplied as the data of the combination of the selected unit component.

An assembly drawing etc. display portion 205 displays an assembly drawing, a full length of the blood circuit, and an amount of filled blood based on the data of the combination of the selection unit components supplied from the unit component selection portion 204 by the use of the blood circuit system database 201. In accordance with the displayed contents such as the assembly drawing, etc., if necessary, as mentioned above, starting from the operation by the unit section assignment section 202, the data of the selected unit in the unit component selection portion 204 is changed. As to the resultant reconfigured blood circuit, the assembly drawing, etc. can be displayed immediately.

FIG. 2 shows an existing standard database 206, an analogous standard retrieving portion 207 and an analogous standard selection portion 208 in addition to the above-mentioned basic configuration.

As mentioned above, the existing standard database 206 is defined as the combination of the unit component constituting the existing specific blood circuit. The existing standard database is constructed by storing a plurality of such existing standards. The analogous standard retrieving portion 207 retrieves the blood circuit analogous to the combination of the selected unit components from the existing database 206 based on the data supplied from the unit component selection portion 204. An analogous standard selection portion 208 has a function of selecting one from the plurality of existing standards retrieved by the analogous standard retrieving portion 207 and supplies the combination data of the selected unit components instead of the data supplied from the unit component selection portion 204 to the assembly drawing etc. display portion 205.

Second Embodiment

Figure 3:
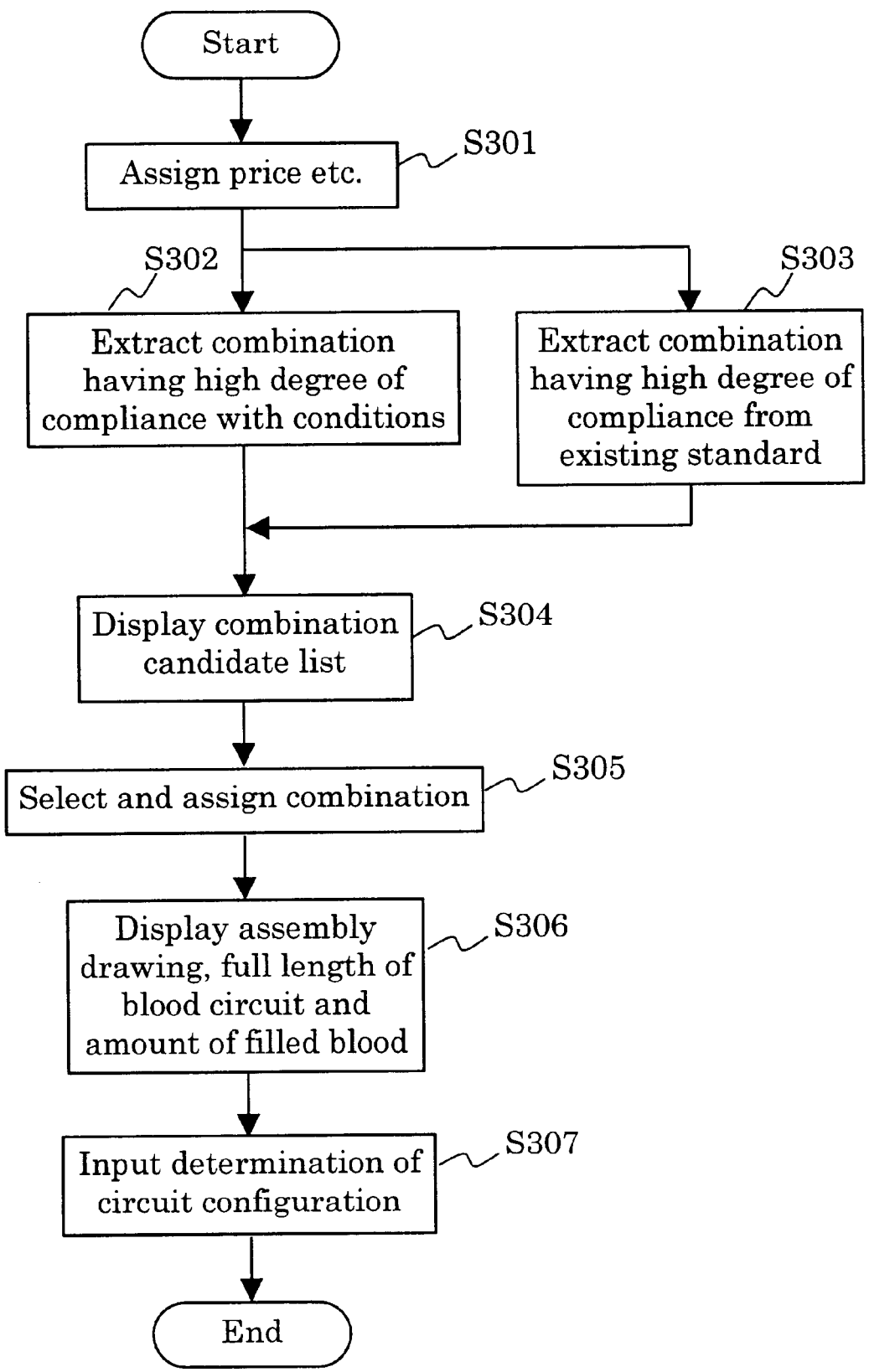
FIG. 3 is a flow chart showing a method of configuring a blood circuit for medical application according to a second embodiment of the present invention.

FIG. 3 is a flow chart showing a method of configuring a blood circuit for medical application of the second embodiment of the present invention. According to the method shown in FIG. 3, unlike the method shown in the first embodiment, a unit component is not selected for each unit section. Instead, conditions such as price etc. are input first, and then the combinations of the unit components satisfying the conditions are extracted from the blood circuit system database, and thus the blood circuit is configured.

Furthermore, the existing standard database described in the first embodiment is constructed and used together with the blood circuit system database. However, this existing standard database is not essential for this embodiment, and therefore can be omitted.

In FIG. 3, first, the set price of the blood circuit is input (step S301). At the same time, it is desirable that in addition to the set price, other set conditions, for example, necessary quantities, desirable delivery period, specification of the circuit and the like can be input.

Next, based on the input set conditions, some of the combinations of the unit components having the highest compliance with the set conditions are extracted by retrieving the blood circuit system database (step S302). The number of extracted combinations may be limited to the appropriate number by giving a higher priority to the combination having higher degree of compliance. Furthermore, the system may be constructed in a manner such that the retrieval is carried out based on the limited item (number) of the above-mentioned set conditions and predetermined priority of the items.

Furthermore, at the same time, from the existing standard database, one having a higher compliance with the set conditions is extracted (step S303). The reason why the retrieving is also carried out in the existing standard is because if the blood circuit is selected from the existing standard it is possible to produce an apparatus in a short time and because the use of the existing unit components can reduce the price.

Next, the retrieved results are displayed as a candidate list (step S304). From the displayed candidates, the combination of the unit components is selected appropriately (step S305). Based on the selected combination, like in the case of FIG. 1, an assembly drawing, the length of the circuit and the amount of filled blood are displayed on the display (step S306). When the content of the displayed blood circuit is within the acceptable range with respect to the set conditions of the blood circuit, an input for determining the configuration of the circuit (step S307) is carried out.

By the method mentioned above, it is possible to determine easily the combination of the unit components constituting the blood circuit, based on the requirements from the economical aspect or productivity aspect.

Figure 4:
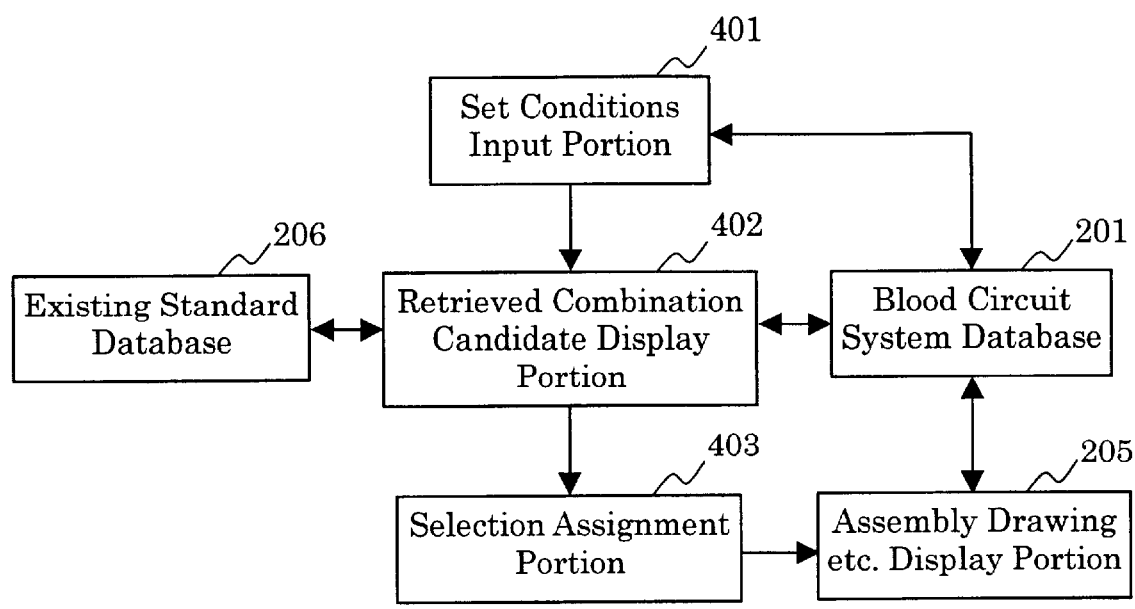
FIG. 4 is a block diagram showing an apparatus for configuring a blood circuit for medical application according to the second embodiment of the present invention.

FIG. 4 shows an apparatus for configuring a blood circuit for medical application for carrying out the above-mentioned method. The blood circuit system database 201, the assembly drawing etc. display portion 205, and the existing standard database 206 are the same as in FIG. 2.

A set conditions input portion 401 has a function for inputting the set conditions such as prices, etc. with respect to the blood circuit to be configured. In the combination candidate retrieving display portion 402, candidates of the combinations of the unit components based on the degree of compliance with the input set conditions by the use of the blood circuit system database 201 are extracted and displayed. The number of the candidates of the combinations of the extracted unit components is limited to an appropriate number by giving a higher priority to higher compliance. The selection assignment portion 403 has a function of selecting one from the candidates of the combinations of the extracted unit components and supplying the extracted candidate to assembly drawing etc. display portion 205 as the data of the combinations of the selected unit components. As mentioned above, a blood circuit is configured based on the set conditions input from the set conditions input portion 401.

In addition to the basic functions, the retrieving of the combination candidates by the combination candidate retrieving display portion 402 is carried out also with respect to the existing standard database 206. Namely, the existing standard having a high compliance with the set conditions is extracted and displayed together with the new combination.

Third Embodiment

It is more practical to configure an apparatus capable of using selectively the method of the first embodiment and the second embodiment instead of using a single method. That is, the configuration method of the blood circuit includes the case where the circuit is intended to be set from the specification of the circuit, and the case where the configuration of the circuit is intended to be selected from the economical aspect such as a price. It is desirable to comply with requests of both cases. Furthermore, by using two methods selectively, it is possible to configure a blood circuit efficiently by taking not only the requirement as the function of the circuit but also the conditions from the business aspect or manufacturing aspect into account.

Figure 5:
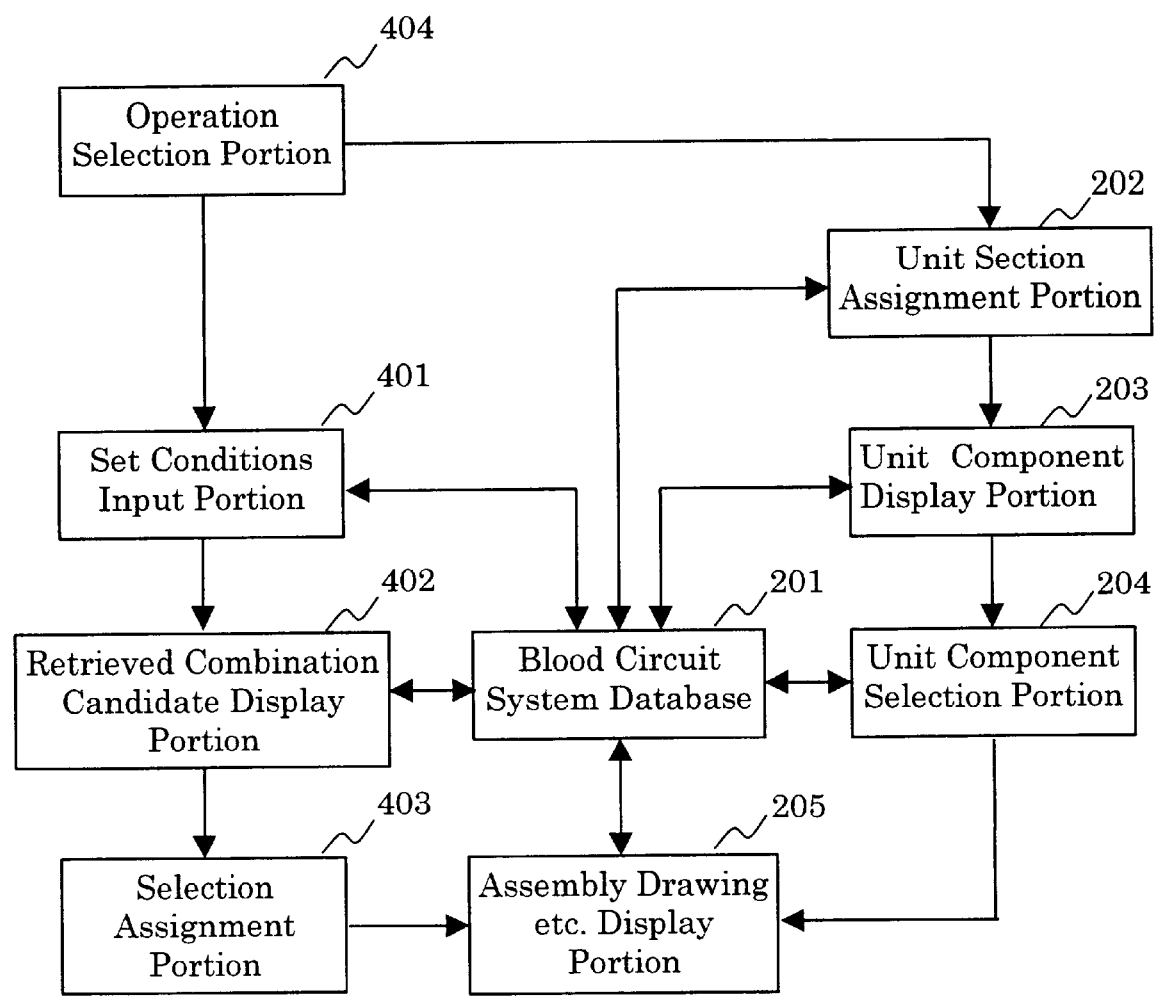
FIG. 5 is a block diagram showing an apparatus for configuring a blood circuit for medical application according to a third embodiment of the present invention.

FIG. 5 shows an apparatus capable of carrying out the two processes, selectively. In this figure, the same element as that shown in FIGS. 2 and 4 is provided with the same reference numeral and the explanation therefor is not repeated herein. Moreover, although in this figure, only the basic functional portions without using an existing standard database are shown, it is possible to configure the apparatus so that the existing standard database further is used.

This apparatus is provided with an operation selection portion 404 capable of selecting an operation by the unit section assignment portion 202 or an operation by the set conditions input portion 401. When the operation by the unit section assignment portion 202 is selected, it is possible to configure the blood circuit by selecting the unit components in each unit section. On the other hand, when the operation by the set conditions input portion 401 is selected, it is possible to configure the blood circuit by appropriately selecting the candidate of the combinations of the unit components based on the input set conditions.

The following are explanations for the formation of the unit sections shown in FIG. 6 in the blood circuit system for medical application used in the above-mentioned embodiments.

Artery Side Circuit

Unit section A: The unit section A includes a tube having a cannula connector connected to an artery side indwelling needle as a main component and also includes a mixing/charging port and a lock-nut connector or a non-locking connector.

Unit section B: The unit section B connects the unit section A and a unit section C and includes a tube for adjusting the length as a main component. A branched tube connector that is connected to the below mentioned unit section D or the unit section E is attached to the unit section B.

Unit section C: The unit section C is located between the unit section B and a dialyzer and includes a liquid feeding pump tube attached directly to a negative pressure detection part and a blood pump apparatus, an artery chamber, a dialyzer connector, and a branched tube connector. A pressure monitor line and a blood level adjusting line are connected to the branched tube connector. A mixing/charging port may be provided in the unit section C.

Unit section D: The unit section D is connected to the branching tube connector of the unit section B or the unit section C, includes a connector capable of being connected to a container containing a blood anticoagulant and has a tube length that is adjusted to the setting location of the blood anticoagulant supply apparatus.

Unit section E: The unit section E is attached to the tip portion of the unit section A, the unit section B, or unit section C. The unit section E is a line used for priming before dialysis or replacement of a drug solution during dialysis. The unit section E includes a connector capable of being connected to a needle for punctuating a drug solution container or other drug solution infusion tool, and a means for opening/closing the line.

Vein Side Circuit

Unit section F: The unit section F is located between the unit section G and a dialyzer, and includes a vein changer being selectable by the dialysis conditions, such as the nature of blood, flow rate of blood or the like, a pressure monitor line, a liquid level adjusting line, and a mixing/charging port.

Unit section G: The unit section G includes a cannula connector connected to a vein side indwelling needle as a main component, and further includes selection units of a plurality of tube diameters, a mixing/charging port, a lock-nut connector or a non-locking connector.

The following are explanations of the examples of each unit component applied to the unit sections A to G.

Unit Section A

FIGS. 7A and 7D show the unit components applied to the unit section A. The unit component A-1 shown in FIG. 7A includes an artery side cannula connector 1, a cover 2 for the artery side cannula connector 1, a blood collecting mixing/charging port 4 and a tube connecting between the artery side cannula connector 1 and the blood collecting mixing/charging port 4. The artery side cannula connector 1 is used for being connected to a scalpel connector such as an indwelling needle inserted into a patient. The blood-collecting mixing/charging port 4 is used for collecting blood for testing or for infusing a drug solution.

The artery cannula connector 1 is covered with the cover 2 at the time of priming and just before the dialysis, as shown in FIG. 7B has the cover 2 taken off and is connected to the indwelling needle 9 (see FIG. 7C). Blood can be collected from the upper part 5 of the mixing/charging port 4.

The unit component A-2 shown in FIG. 7D is provided with a lock nut between the artery side cannula connector 1 and the mixing/charging port 4 of the unit component A-1. Numeral 8 denotes a connecting line. The lock nut 6 is temporarily fixed to a lock portion 7 when it is not used. However, as shown in FIG. 7E, it can be shifted to the location of the artery side cannula connector 1 by hand. Since the screw is provided inside the lock nut 6, it can be connected to the artery side cannula connector 1 so as to be locked to a winged indwelling needle 9 (see FIG. 7F).

Unit Section B

FIGS. 8A to 8D show unit components applied to the unit section B.

First, a unit component B-1-1 is a resin tube 11 having a full length of about 600–1000 mm (FIG. 8A). A unit component B-1-2 is a resin tube 12 having a full length of about 1000–1600 mm (FIG. 8).

In the case where the drug solution is replaced from the branched tube branching for fluid replacement in this unit section B, as shown in the unit component B-2-1 (FIG. 8) and the unit component B-2-2 (FIG. 8D), a tube provided with a branched tube connector 13 is used.

Unit Section C

FIGS. 9A to 9D show the unit components useful for the unit section C. A unit component C-1-1 (FIG. 9A) is provided with a pump tube 21 having an outer diameter of 12 mm and a length of about 250–350 mm, and an artery chamber 23 including a mesh filter 24. The artery chamber 23 is an element for pulling out the air entering the dialyzer in order to prevent the contamination of the blood by air. Numeral 25 is a branched tube connector, 26 denotes a dialyzer connector, and 27 denotes a negative pressure detection portion. The negative pressure detection portion 27 is a portion for informing abnormality when it is broken at the time of deficiency in removing the blood during the dialysis. The branched tube connector 25 may be used only by attaching the liquid solution replacement line or a drug solution infusion line.

A unit component C-1-2 (FIG. 9B) is provided with a pump tube 22 having an outer diameter of 10 mm and a length of about 250–350 mm, and an artery chamber 23 including a mesh filter 24 like the unit component C-1-1.

Similar to the unit component C-1-1, the unit component C-2-1 (FIG. 9C) is provided with a pump tube 22 having an outer diameter of 12 mm and a length of about 250–350 mm, and an artery chamber 29. However, in the unit component C-2-1, the artery chamber 29 does not have a mesh filter for miniaturization.

Similar to the unit component C-1-2, the unit component C-2-2 (FIG. 9D) is provided with a pump tube 22 having an outer diameter of 10 mm and a length of about 250–350 mm, and an artery chamber 29. However, in this component, the artery chamber 29 does not have a mesh filter for miniaturization.

In any of the types, a small-diameter tube 28 may be used for a main line so as to reduce the priming amount.

Unit Section D

Figure 10A:
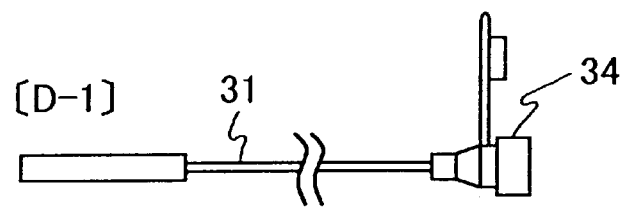
FIGS. 10A to 10C are plan views showing examples of unit components applied to a unit section D.
Figure 10B:
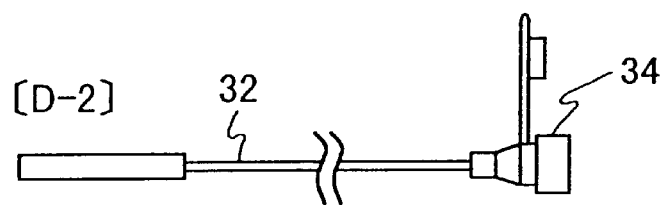
Figure 10C:
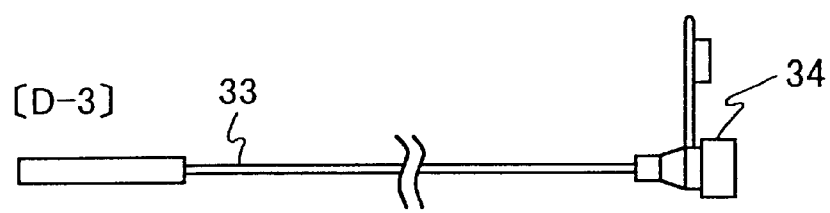
Figure 13A:
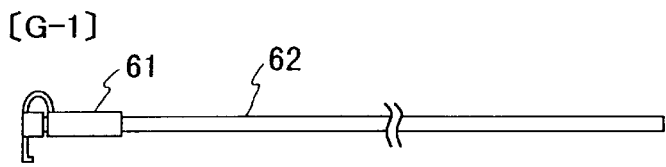
FIGS. 13A to 13D are plan views showing examples of unit components applied to a unit section G.
Figure 13B:
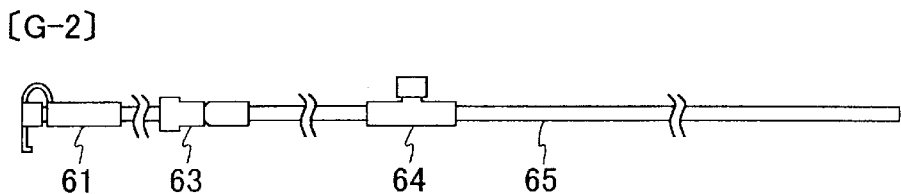
Figure 13C:
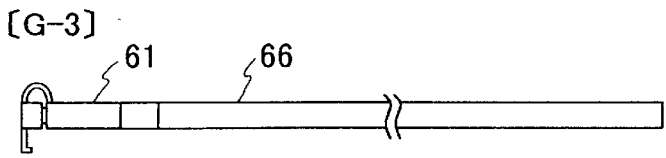
Figure 13D:
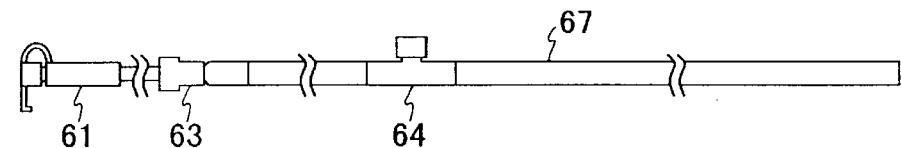

FIGS. 10A to 10C show the unit components applied to the unit section D.

A unit component D-1 (FIG. 10A) is an anticoagulant infusion line provided with a tube 31 having a full length of about 200–400 mm and an outer diameter of about 1.5–4 mm and a connector 34 that can be connected to a container containing a blood anticoagulant. The anticoagulant infusion line is used for infusing drug preventing the coagulation of the blood during the dialysis. This unit component can prevent the excessive absorption of the drug solution due to negative pressure by arranging it behind the pump tube. For example, the unit component can be connected to the branched tube connector 25 of the unit component C-1-1 shown in FIG. 9A.

A unit component D-2 (FIG. 10B) is an anticoagulant infusion line provided with a tube 32 having a full length of about 400–600 mm and an outer diameter of about 1.5–4 mm and a connector 34 that can be connected to a container containing a blood anticoagulant. The unit component D-2 matches to a console set-up type syringe pump and is the most suitable for the general dialysis.

A unit component D-3 (FIG. 10C) is an anticoagulant infusion line provided with a tube 33 having a full length of about 600–1000 mm and an outer diameter of about 1.5–4 mm and a connector 34 that can be connected to a container containing a blood anticoagulant.

Unit Section E

FIGS. 11A to 11D show the unit components applied to the unit section E.

The unit component E-1-1 (FIG. 11A) is a straight type liquid replacement line for a drug solution. Numeral 41 denotes a drip infusion cylinder, 42 denotes a roller clamp, and 43 denotes a connector portion that is connected to a needle for puncturing a container for a drug solution. This type is a line used in a manner in which it is attached to the unit section B or C. The drip infusion cylinder 41 is provided so that the flow state can be observed, and the roller clamp 42 is provided for adjusting the flow rate.

A unit component E-1-2 (FIG. 11B) is a Y-shaped liquid replacement line and is provided with a Y-shaped branching line having a stopper 44 and a connector 45.

A unit component E-1-3 (FIG. 11C) is a port for liquid replacement and includes a stopper 44, a needle for puncturing a drug solution container or a connector 45 capable of being connected to another drug solution infusion tool.

A unit component E-2-1 (FIG. 11D) is a straight type liquid replacement line having a connector 43 that is connected to a stopper 44 and a needle for puncturing a drug solution container. Unlike the above-mentioned three unit sections, this type is connected to the tip portion of the unit section A.

Unit Section F

FIGS. 12A and 12B show unit components fit for the unit section F.

A unit component F-1 (FIG. 12A) is a unit component having a vein chamber 51 having a length of about 100–150 mm and including a mesh filter 53. The vein chamber 51 is used for preventing the air from entering when the purified blood is fed back to the body of a patient. Numeral 54 is a mixing/charging port, 55 denotes a connector connected to a dialyzer, 56 denotes a pressure monitor connecting portion, and 57 denotes a liquid level adjusting portion.

A unit component F-2 (FIG. 12B) has a vein chamber 52 including a mesh filter 53 and has a length of about 100 to 170 mm.

Unit Section G

FIGS. 13A to 13D show the unit components fit for the unit section G.

A unit component G-1 (FIG. 13A) includes a vein side cannula connector covered with a cover 61 and a small-diameter tube 62 having a full length of about 1400–1800 mm and an inner diameter of about 3.5 mm. Similar to the artery side, a priming amount and waste can be reduced by using the small-diameter tube. The vein side cannula connector is to be connected to a scalpel connector such as an indwelling needle inserted into a patient.

Similarly, a unit component G-2 (FIG. 13B) includes a vein side cannula connector and a small-diameter tube 65 having a full length of about 1800–2400 mm and an inner diameter of about 3.5 mm. The unit component G-2 further includes a blood connecting mixing/charging port 64 and a lock nut 63.

Similarly, a unit component G-3 (FIG. 13C) includes a vein side cannula connector and a large-diameter tube 66 having a full length of about 1400–1800 mm and an inner diameter of about 4.5 mm.

Similarly, a unit component G-4 (FIG. 13D) includes a vein side cannula connector and a large-diameter tube 67 having a full length of about 1800–2400 mm and an inner diameter of about 4.5 mm, and further includes a blood collecting mixing/charging port 64 and a lock nut 63.

Although, in FIGS. 13A to 13D, only four kinds of unit components are shown, the number of the unit components prepared in this example becomes 16, when calculated by combining all of the elements including a size of the inner diameter of the tube, the length of the tube, existence and nonexistence of the lock nut, and existence and nonexistence of the mixing/charging port. The number of the unit components is greater as compared with the other unit section, however, the cannula connector is automatically determined by selecting the unit component A, and also the length can be automatically determined by selecting the unit section B.

Moreover, it is preferable in the method of configuring a blood circuit for medical application that the number of the unit sections to be divided is 4 to 10 in total, because the number in such a range is suitable to be divided. That is, the unit is divided into an artery side and a vein side, and both the artery side circuit and the vein side circuit are respectively divided into a plurality of sections so as to be provided with a variation. As a result, the blood circuit has four or more of the unit sections. On the other hand, from the viewpoint of the advantages in the safety and productivity, the number of the unit components should be relatively small. Therefore, the number of the unit sections is at most 10 and desirably about 7.

Moreover, the number of the unit components included in each unit section is desired to be in the range from 2 to 5 from the viewpoint of the variations and standard unification. Furthermore, it is particularly preferable that the number of the unit components including the vein side cannula connector is 2 to 20 and the number of the other unit components is 2 to 5. The reason why the number of the number of the unit components including the vein side cannula connector is larger is because it is necessary to prepare the different kinds of tubes having different inner diameters with respect to the returning the blood and it is necessary to prepare the different kinds of tubes for the blood collection and the infusion of the drug solution at the vein side. In general, since the same type connectors are used for the artery side cannula connector and the vein side cannula connector, the vein side component may be determined simultaneously by selecting a component at the side of the artery side. Therefore, a large number of unit components does not lead to the complication of the system necessarily.

As mentioned above, by configuring the blood circuit system while considering the safety in the field of the medical field and the production site and the function in advance, the total standard of the complicated circuit can be integrated efficiently. Thereby, the automation at the production site can be realized, to thus supplying the products cheaply.

As mentioned above, according to the present invention, based on the systematized blood circuit system, it is possible to configure the blood circuit in accordance with the application of use. Furthermore, the operation of checking the compliance with the desired specification or not can carried out efficiently without assembling the sample actually. Furthermore, in a case where it is not fit for the desired specification, the blood circuit is reconfigured by altering the unit components, and checking thereof is carried out extremely easily. Furthermore, by displaying the entire circuit, the circuit can be grasped as a whole and necessary and unnecessary elements can be confirmed and the necessary elements can be prevented from missing.

The invention may be embodied in other forms without departing from the spirit or essential characteristics thereof. The embodiments disclosed in this application are to be considered in all respects as illustrative and not limitative, the scope of the invention is indicated by the appended claims rather than by the foregoing description, and all changes which come within the meaning and range of equivalency of the claims are intended to be embraced therein.

What is claimed is:

1. A method of configuring a blood circuit for medical application, the blood circuit being configured by forming a blood circuit system in which a blood circuit is divided into a plurality of unit sections and a plurality of selectable unit components are prepared for at least one unit section, selecting at least one unit component from each unit section based on the formed blood circuit system, and combining the selected unit components; the method comprising:

using a blood circuit system database in which data with respect to the unit sections and the unit components contained in the blood circuit system are stored, inputting one of the unit sections on a basis of the blood circuit system database as an assigned unit section to the computer, extracting the data of a plurality of the corresponding unit components from the blood circuit system database by the computer based on the input assigned unit section, and displaying the extracted data on a display, inputting one component selected from the displayed unit components as a selected unit component to the computer, after carrying out the above-mentioned procedures in the necessary unit section, by the use of the blood circuit system database, displaying an assembly drawing showing an entire configuration of the blood circuit obtained by combining the input selected unit components and at least one of a full length of the blood circuit or an amount of filled blood on a display, and then inputting a command for changing the selection of the unit components or a command for determining the configuration of the blood circuit in the computer.

2. The method of configuring a blood circuit for medical application according to claim 1, further comprising, after the procedure of inputting the selected unit components to the computer, selectively either returning to the procedure for inputting the assigned unit section or inputting a selection terminating command for terminating the input of the selected unit components and going to the following procedures, when the selection terminating command is input, if there is any unit section with no selected unit component input, returning to the procedure of inputting the assigned unit section, and if the selected unit component has been input in all the unit sections, going to the following procedures, and if the selection of the unit component is to be changed, returning to the procedures of inputting the assigned unit section.

3. The method of configuring a blood circuit for medical application according to claim 1, wherein if the command of determining the configuration of the blood circuit is input, based on the blood circuit system database, the price of the blood circuit obtained by combining each selected unit component is displayed on the display.

4. The method of configuring a blood circuit for medical application according to claim 1, wherein an existing standard database in which a plurality of existing standards are stored is further used, the existing standard being the combination of the unit components constituting an existing specific blood circuit, and when an assembly drawing, a full length of the blood circuit and an amount of filled blood are displayed, the existing standard analogous to the configuration of the displayed blood circuit is retrieved and displayed as an analogous standard.

5. The method of configuring a blood circuit for medical application according to claim 1, wherein the blood circuit for medical application is a blood circuit for dialysis, and the blood circuit is divided into an artery side circuit and a vein side circuit and further each of the artery side circuit and the vein side circuit is divided into a plurality of unit sections.

6. An apparatus for configuring a blood circuit for medical application, the blood circuit being configured by forming a blood circuit system in which a blood circuit is divided into a plurality of unit sections and a plurality of selectable unit components are prepared for at least one unit section, selecting at least one unit component from each unit section based on the formed blood circuit system, and combining the selected unit components, comprising:

a blood circuit system database in which data with respect to the unit sections and the unit components contained in the blood circuit system are stored, a unit section assignment portion for inputting one unit section on the basis of the blood circuit system database as an assigned unit section, a unit component display portion for extracting data of a plurality of the unit components corresponding to the input assigned unit section and displaying the extracted data on a display, a unit component selection portion for inputting one unit component selected from the displayed unit components, maintaining the data of the selected unit components of all the unit sections, and supplying the maintained data as data of the combination of the selected unit components, and an assembly drawing etc. display portion of displaying an assembly drawing showing an entire configuration of the blood circuit and at least one of a full length of the blood circuit or an amount of a filled blood on the display by using the blood circuit system database based on the data of the combination of the selected unit components, wherein the data of the selected unit components in the unit component selection portion can be changed by assigning the unit section in the unit section assignment portion.

7. The apparatus for configuring a blood circuit component according to claim 6, further comprising:

an existing standard database in which a plurality of the existing standards are stored, the existing standard being the combination of the unit components constituting an existing specific blood circuit, an analogous standard retrieving portion of retrieving a blood circuit that is analogous to the combination of the selected unit components from the existing standard database on a basis of the data supplied from the unit component selection portion, and an analogous standard selection portion having a function of selecting one from the retrieved existing standards by the analogous standard retrieving portion, and supplying, instead of in the unit component selection portion, the data of the combinations of the selected unit components on the basis of the selected existing standard to the assembly drawing etc. display portion.

* * * * *